(12) United States Patent
Osadchy et al.

(10) Patent No.: US 6,335,617 B1
(45) Date of Patent: ***Jan. 1, 2002

(54) METHOD AND APPARATUS FOR CALIBRATING A MAGNETIC FIELD GENERATOR

(75) Inventors: Daniel Osadchy, Haifa; Assaf Govari, Qiryat Haim, both of (IL)

(73) Assignee: Biosense, Inc., New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,244
(22) PCT Filed: May 5, 1997
(86) PCT No.: PCT/IL97/00146
  § 371 Date: Mar. 8, 1999
  § 102(e) Date: Mar. 8, 1999
(87) PCT Pub. No.: WO97/42517
  PCT Pub. Date: Nov. 13, 1997

Related U.S. Application Data

(60) Provisional application No. 60/016,908, filed on May 6, 1996.

(51) Int. Cl.⁷ ........................ G01R 35/00; G01R 33/02; A61B 5/05
(52) U.S. Cl. ........................ 324/202; 324/247; 702/85
(58) Field of Search ............................ 324/202, 207.12, 324/207.17, 207.23, 207.26, 225, 239, 244, 246, 260, 320; 73/1.01, 1.79; 702/85, 94, 95, 104

(56) References Cited

U.S. PATENT DOCUMENTS

| 3,361,963 A | 1/1968 | Watson |
| 3,644,825 A | 2/1972 | Davis, Jr. et al. ............. 324/41 |
| 3,868,565 A | 2/1975 | Kuipers .................... 324/34 R |
| 4,017,858 A | 4/1977 | Kuipers .................. 343/100 R |
| 4,054,881 A | 10/1977 | Raab ...................... 343/112 R |

(List continued on next page.)

FOREIGN PATENT DOCUMENTS

| DE | 43 25 059 A | 1/1994 | |
| WO | WO 92/03090 | 3/1992 | ............ A61B/5/06 |
| WO | WO 94/04938 | 3/1994 | ............ G01S/3/14 |
| WO | WO 94/23647 | 10/1994 | ............ A61B/5/05 |
| WO | WO 96/05768 | 2/1996 | ............ A61B/5/06 |

(List continued on next page.)

OTHER PUBLICATIONS

Hideo Saito Et Al.: "Magnetic Field Imaging Using Computer Tomography–Vector Reconstruction", Systems & Computers in Japan, US, Scripta Technica Journals. New York, Vol. 21, No. 13, 1990, pp. 69–78.
Supplementary European Search Report for EP 97 91 8323.

*Primary Examiner*—Walter E. Snow
(74) *Attorney, Agent, or Firm*—Louis J. Capezzuto

(57) ABSTRACT

A method for calibrating a magnetic field generator, including fixing one or more magnetic field sensors to a probe in known positions and orientations and selecting one or more known locations in the vicinity of the magnetic field generator. The magnetic field generator is driven so as to generate a magnetic field. The probe is moved in a predetermined, known orientation to each of the one or more locations, and signals are received from the one or more sensors at each of the one or more locations. The signals are processed to measure the amplitude and direction of the magnetic field, at the respective positions of the one or more sensors and to determine calibration factors relating to the amplitude and direction of the magnetic field in the vicinity of the magnetic field generator.

17 Claims, 4 Drawing Sheets

U.S. PATENT DOCUMENTS

| | | | |
|---|---|---|---|
| 4,317,078 A | 2/1982 | Weed et al. ................. 324/208 |
| 4,560,930 A | 12/1985 | Kouno ....................... 324/207 |
| 4,613,866 A | 9/1986 | Blood ........................ 343/448 |
| 4,642,786 A | 2/1987 | Hanson ..................... 364/559 |
| 4,651,436 A | 3/1987 | Gaal ............................ 33/533 |
| 4,710,708 A | 12/1987 | Rorden et al. .............. 324/207 |
| 4,771,237 A | 9/1988 | Daley |
| 4,849,692 A | 7/1989 | Blood ........................ 324/208 |
| 4,905,698 A | 3/1990 | Strohl, Jr. et al. ...... 128/653 R |
| 4,945,305 A | 7/1990 | Blood ................... 324/207.17 |
| 5,002,137 A | 3/1991 | Dickinson et al. ............ 175/19 |
| 5,042,486 A | 8/1991 | Pfeiler et al. ............ 128/653 R |
| 5,068,608 A | 11/1991 | Clark, Jr. .................... 324/220 |
| 5,099,845 A | 3/1992 | Besz et al. ............... 128/653.1 |
| 5,172,056 A | 12/1992 | Voisin ................... 324/207.17 |
| 5,211,165 A | 5/1993 | Dumoulin et al. ....... 128/653.1 |
| 5,251,635 A | 10/1993 | Dumoulin et al. ....... 128/653.1 |
| 5,253,647 A | 10/1993 | Takahashi et al. ....... 128/653.1 |
| 5,255,680 A | 10/1993 | Darrow et al. ........... 128/653.1 |
| 5,265,610 A | 11/1993 | Darrow et al. ........... 128/653.1 |
| 5,269,289 A | 12/1993 | Takehana et al. .............. 128/4 |
| 5,273,025 A | 12/1993 | Sakiyama et al. ............... 128/6 |
| 5,309,913 A | 5/1994 | Kormos et al. .......... 128/653.1 |
| 5,325,873 A | 7/1994 | Hirshi et al. ................ 128/899 |
| 5,375,596 A | 12/1994 | Twiss et al. ............. 128/653.1 |
| 5,377,678 A | 1/1995 | Dumoulin et al. ....... 128/653.1 |
| 5,425,367 A | 6/1995 | Shapiro et al. .......... 128/653.1 |
| 5,425,382 A | 6/1995 | Golden et al. .............. 128/899 |
| 5,429,132 A | 7/1995 | Guy et al. ................ 128/653.1 |
| 5,437,277 A | 8/1995 | Dumoulin et al. ........ 128/653.1 |
| 5,443,489 A | 8/1995 | Ben-Haim .................. 607/115 |
| 5,453,687 A | 9/1995 | Zierdt et al. ........... 324/207.17 |
| 5,497,082 A | 3/1996 | Hancock |
| 5,558,091 A | 9/1996 | Acker et al. |
| 5,577,502 A | 11/1996 | Darrow et al. ........... 128/653.1 |
| 5,622,169 A | 4/1997 | Golden et al. ........... 128/653.1 |
| 5,682,886 A | 11/1997 | Delp et al. ............... 128/653.1 |
| 5,694,945 A | 12/1997 | Ben-Haim .................. 128/736 |
| 5,715,822 A | 2/1998 | Watkins et al. .......... 128/653.5 |
| 5,729,129 A * | 3/1998 | Acker .................... 324/207.12 |
| 5,752,513 A | 5/1998 | Acker et al. ............. 128/653.1 |
| 5,769,843 A | 6/1998 | Abela et al. ................... 606/10 |

FOREIGN PATENT DOCUMENTS

| | | | | |
|---|---|---|---|---|
| WO | WO 96/41119 | 12/1996 | ............ G01B/7/14 |
| WO | WO 97/29678 | 8/1997 | |
| WO | WO 97/29709 | 8/1997 | ............ A61B/19/00 |
| WO | WO 97/29710 | 8/1997 | ............ A61B/19/00 |
| WO | WO 97/32179 | 9/1997 | ............ G01B/7/14 |

* cited by examiner

METHOD AND APPARATUS FOR CALIBRATING A MAGNETIC FIELD GENERATOR

This application claims the benefit of U.S. Provisional Patent Application No. 60/016,908, filed May 6, 1996, which is incorporated herein by reference.

FIELD OF THE INVENTION

The present invention relates generally to apparatus for generating and detecting electromagnetic fields, and specifically to non-contact, electromagnetic methods and devices for tracking the position and orientation of an object.

BACKGROUND OF THE INVENTION

Non-contact electromagnetic tracking systems are well known in the art, with a wide range of applications.

For example, U.S. Pat. No. 4,054,881, incorporated herein by reference, describes a tracking system using three coils to generate electromagnetic fields in the vicinity of the object. The fields generated by these three coils are distinguished from one another by open loop multiplexing of time, frequency or phase. The signal currents flowing in three orthogonal sensor coils are used to determine the object's position, based on an iterative method of computation.

Other electromagnetic tracking systems are described in U.S. Pat. Nos. 3,644,825, 3,868,565, 4,017,858 and 4,849,692, whose disclosures are likewise incorporated herein by reference.

U.S. Pat. No. 5,391,199, to Ben-Haim, which is incorporated herein by reference, describes a system for generating three-dimensional location information regarding a medical probe or catheter. A sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT patent publication No. WO96/05768, whose disclosure is incorporated herein by reference, describes a system that generates six-dimensional position and orientation information regarding the tip of a catheter. This system uses a plurality of non-concentric sensor coils adjacent to a locatable site in the catheter, for example near its distal end, and a plurality of radiator coils fixed in an external reference frame. The sensor coils generate signals in response to magnetic fields generated by the radiator coils, which signals allow for the computation of six location and orientation coordinates.

Radiator coils with cores are known in position sensing systems. The cores increase the field output of the coils, but they tend to distort the fields, and therefore reduce the accuracy of position detection. The theory of magnetic fields generated by radiator coils with cores is known in the art, as described, for example, by John David Jackson in *Classical Electrodynamics,* Second Edition (1975), pages 168–208, which is incorporated herein by reference. In practice, however, it is difficult to derive a theoretical model that will accurately predict the magnetic field generated by a coil with a core.

Ferrite cores are advantageous, because they have both high magnetic permeability ($\mu$) and high resistivity ($\rho$). Due to the high resistivity, the cores can be used with a time-varying (AC) magnetic field without inducing eddy currents in the cores, which further distort and complicate the magnetic field. The Polhemus position-sensing system, as described, for example, in U.S. Pat. No. 4,017,858, uses such ferrite cores in its (AC) radiators. Ferrite materials are relatively expensive and fragile, however, making them impractical and uneconomic for use in sizes over about 5 cm in diameter.

Soft iron cores are also effective in increasing magnetic field output of a coil, but they cause serious distortion of AC magnetic fields due to eddy currents generated in the core by the coil. The Ascension position-sensing system, described in U.S. Pat. No. 4,849,692, is based on a DC magnetic field, and can therefore use soft iron cores in its DC radiator coils, since no eddy currents are generated by the DC field.

SUMMARY OF THE INVENTION

The accuracy and efficacy of electromagnetic tracking systems, such as those cited above, is generally dependent on precise knowledge of the distribution of the magnetic fields generated by the radiator coils. Although these fields may be calculated theoretically, based on the geometry of the coils, the actual magnetic fields typically differ from the theoretical models. For example, the fields may differ from the models due to small deviations in the manufacture of the coils. In the case of coils having a ferromagnetic core, the geometry and electrical and magnetic properties of the core must also be taken into account. There will typically be greater deviations from the theoretical models due, for example, to nonlinearities, hysteresis and eddy currents in the core, and to imprecise location of the core relative to the coils. These deviations may lead to inaccuracies in determining the position and orientation of the object being tracked. It would, therefore, be desirable to calibrate the radiator coils by precise measurement of the direction and amplitude of the magnetic field in the vicinity of the object to be tracked.

It is thus an object of some aspects of the present invention to provide a method and apparatus for calibrating electromagnetic radiator coils or other types of magnetic field generators.

In some aspects of the present invention, the field equations of an electromagnetic radiator coil are used to derive a parametric, theoretical model of the field, which is compared with calibration measurements of the field to determine accurate values of the parameters.

In one aspect of the present invention, the theoretical model takes into account perturbations of the field due to the effect of a ferromagnetic core in the radiator coil.

In another aspect of the present invention, the radiator coils are used as part of an object tracking system, such as a system for use in determining the position and orientation of a probe inside the body of a subject during a medical or surgical procedure.

In preferred embodiments of the present invention, apparatus for calibrating magnetic field generators comprises at least one sensor coil, fixed to a positioning device in a known geometrical relation. The positioning device, which may be of any suitable type known in the art, is adapted to position the at least one sensor coil in one or more known positions in a vicinity of the field generator being calibrated. The at least one sensor coil generates electrical signals in the presence of a time-varying magnetic field, which signals are analyzed to determine the direction and amplitude of the magnetic field at the positions of the coils.

In some preferred embodiments of the present invention, the at least one sensor coil comprises a plurality of sensor coils, preferably including three non-concentric coils, which are mutually substantially orthogonal, and are fixed in a predetermined mutual spacing. Non-concentric coils are advantageous in that they may more readily be wound in a small volume, preferably 1 mm$^3$ or less, desired for use in accordance with the present invention.

In some of these preferred embodiments, the coils are fixed in a substantially linear arrangement. Preferably the positioning device positions the coils successively in a plurality of positions along an axis defined by the arrangement of the coils. In one such preferred embodiment, the three non-concentric coils are fixed in a probe substantially as described in PCT patent application No. PCT/US95/01103, whose disclosure is incorporated herein by reference.

In other preferred embodiments of the present invention, the coils are fixed to respective faces of a cube. In one such preferred embodiment, six coils are respectively fixed to the six faces of the cube, such that the axis of each of the coils is orthogonal to the respective face to which it is fixed. Preferably, the positioning device positions the cube in a plurality of positions on a grid defined by the arrangement of the coils on the cube.

In preferred embodiments of the present invention, a method for calibrating a magnetic field generator comprises placing at least one sensor coil in one or more known positions and orientations in a vicinity of the field generator, driving the field generator to generate a time-varying magnetic field, and measuring the electrical signals generated by the at least one sensor coil, so as to determine the direction and amplitude of the magnetic field at the one or more known positions. The coil may have an air core or, preferably, a ferromagnetic core.

In some preferred embodiments of the present invention, wherein the field generator is substantially rotationally symmetrical about an axis thereof, the method for calibrating the field generator includes defining a calibration plane having a first axis defined by an axis of rotational symmetry of the field generator and a second axis chosen to be orthogonal to the first axis. Preferably the second axis is in a plane defined by the field generator. The at least one sensor coil is then placed in one or more known positions that are substantially within a quadrant of this plane, defined by the first and second axes, and the directions and amplitudes of the magnetic fields are determined in this quadrant. Due to the substantial symmetry of the field generator, the directions and amplitudes of the magnetic field determined in this quadrant are sufficient to determine the directions and amplitudes of the magnetic field in any other quadrant defined by choosing another second axis orthogonal to the first axis.

In a preferred embodiment of the present invention, the method for calibrating a field generator includes fixing three sensor coils to a positioning device in known, mutually substantially orthogonal orientations and in known positions in a non-concentric, substantially linear arrangement. The positioning device is used to place the coils successively in a plurality of known positions along a first axis defined by the arrangement of the coils. The electrical signal generated by each of the three sensor coils at each of the plurality of positions along this first axis is used to determine the amplitude of the component of the magnetic field projected along the direction of orientation of the respective sensor coil. Three such component amplitudes are thus determined at each of the plurality of positions, so that the magnetic field is completely determined along the first axis. The positioning device is then shifted to one or more additional axes, parallel to and in known displacement relative to the first axis, and the steps described above are repeated so as to determine the magnetic fields along these additional axes.

Alternatively, in another preferred embodiment of the present invention, fixing the three sensor coils comprises fixing a position sensing device including three sensor coils, substantially as described in the above-mentioned PCT patent application No. PCT/US95/01103. Position signals received from the device at each of the plurality of known positions in the vicinity of the field generator are compared with the actual, known position coordinates, so as to generate a calibration function.

In other preferred embodiments of the present invention, the at least one sensor coil is used to make additional measurements in both the calibration plane, as described above, and one or more additional planes, preferably having the same first axis as the calibration plane, but having different, respective second axes. Such additional measurements are useful in calibrating the field generator when the field may deviate from rotational symmetry, due, for example, to asymmetry and/or eccentricity of a ferromagnetic core within the radiator.

In still other preferred embodiments of the present invention, the at least one sensor coil is used to make measurements of the direction and amplitude of the magnetic field at a grid of points in the vicinity of the field generator.

There is therefore provided, in accordance with a preferred embodiment of the present invention, a method for calibrating a magnetic field generator, including:

fixing one or more magnetic field sensors to a probe in known positions and orientations;

selecting one or more known locations in a vicinity of the magnetic field generator;

driving the magnetic field generator so as to generate a magnetic field;

moving the probe in a predetermined, known orientation to each of the one or more locations;

receiving signals from the one or more sensors at each of the one or more locations;

processing the signals to measure the amplitude and direction of the magnetic field, at the respective positions of the one or more sensors; and determining calibration factors relating to the amplitude and direction of the magnetic field in the vicinity of the magnetic field generator.

Preferably, fixing one or more magnetic sensors to a probe includes fixing sensor coils to the probe. Two or more sensor coils are preferably fixed to the probe, in orientations such that respective axes of the coils are mutually substantially orthogonal.

Preferably, fixing one or more magnetic sensors to a probe includes fixing three sensors to the probe, such that the positions of the sensors on the probe are substantially collinear.

Alternatively, fixing one or more magnetic sensors to the probe includes fixing sensors to a cube.

Preferably, selecting one or more known locations includes selecting a plurality of locations, and moving the probe includes moving the probe along an axis defined by the positions of the sensors on the probe and passing through two or more of the plurality of locations, preferably in steps of substantially equal length, such that the distance between any two of the sensors is substantially integrally divisible by the length of the steps.

Preferably, for calibrating a magnetic field generator that is substantially rotationally symmetrical, selecting the one or more known locations includes selecting one or more locations in a quadrant defined by the axis of rotational symmetry of the magnetic field generator and by a second axis in a plane defined by the magnetic field generator and normal to the axis of rotational symmetry, and moving the probe includes orienting the probe so that the one or more sensors are positioned in the plane.

Determining calibration factors preferably includes calculating theoretical values of the amplitude and direction of the magnetic field generated by the magnetic field generator at the one or more known locations; comparing the theoretical values to the amplitude and direction of the magnetic field measured at said locations; and computing arithmetic factors corresponding to the difference between the theoretical values and the measured amplitude and direction of the magnetic field at each such location.

Preferably, computing arithmetic factors includes fitting the theoretical values to the measured amplitude and direction of the field.

Preferably, calculating theoretical values includes deriving a theoretical model of the magnetic field in the presence of an air core within the magnetic field generator, and modifying the model to account for the presence of a ferromagnetic core within the magnetic field generator.

Alternatively or additionally, modifying the model includes determining a perturbation of the field due to a the core, preferably by determining a perturbation due to a nonlinearity of the core or, further additionally or alternatively, by determining a perturbation due to eddy currents in the core.

In a preferred embodiment, the method described above further includes fixing a magnetic-field-responsive position-sensing device to an object; placing the object in the vicinity of the magnetic field generator; receiving signals from the position-sensing device; processing the signals so as to calculate the position or orientation of the object; and applying the calibration factors so as to improve the accuracy of calculation of the position or orientation.

Preferably, calibrating the magnetic field includes storing the calibration factors in a memory associated with the radiator coil.

There is further provided, in accordance with a preferred embodiment of the present invention, apparatus for calibrating a magnetic field generator including:
 a plurality of magnetic field sensors, which generate electrical signals in response to magnetic fields applied thereto by the field generator; and
 a positioning device, for moving the sensors,
 wherein the sensors are fixed to the positioning device in a substantially linear arrangement, and
 wherein the positioning device has an axis of motion that is parallel to an axis defined by the substantially linear arrangement of the coils.

Preferably, the magnetic field sensors include sensor coils, which are fixed so that respective axes of the coils are mutually substantially orthogonal.

Preferably, the magnetic field sensors are fixed to the positioning device in a substantially linear arrangement.

Alternatively, the magnetic field sensors include sensors which are fixed to the faces of a cube, which is fixed to the positioning device.

Preferably, the sensor coils generate signals which are received by a computer which compares the signals to a theoretical model, so as to calibrate the magnetic field generator.

There is also provided, in accordance with a preferred embodiment of the present invention, a calibrated magnetic field generator, including:
 at least one coil, which is driven to generate the magnetic field; and
 an electronic memory circuit, associated with the at least one coil, for storing calibration factors relating to the field generated by the coil.

Preferably, the field generator includes a core inside the at least one coil, most preferably a ferromagnetic core. Preferably, the ferromagnet includes a ferrite, or alternatively, soft iron.

Preferably, the field generator includes an electronic memory circuit, most preferably an EPROM.

Preferably, the calibration factors relate the field generated by the at least one coil to a theoretical model thereof.

Preferably, the calibration factors include look-up tables.

BRIEF DESCRIPTION OF THE DRAWINGS

The present invention will be more fully understood from the following detailed description of the preferred embodiments thereof, taken together with the drawings in which.

DETAILED DESCRIPTION OF PREFERRED EMBODIMENTS

Figure 1:
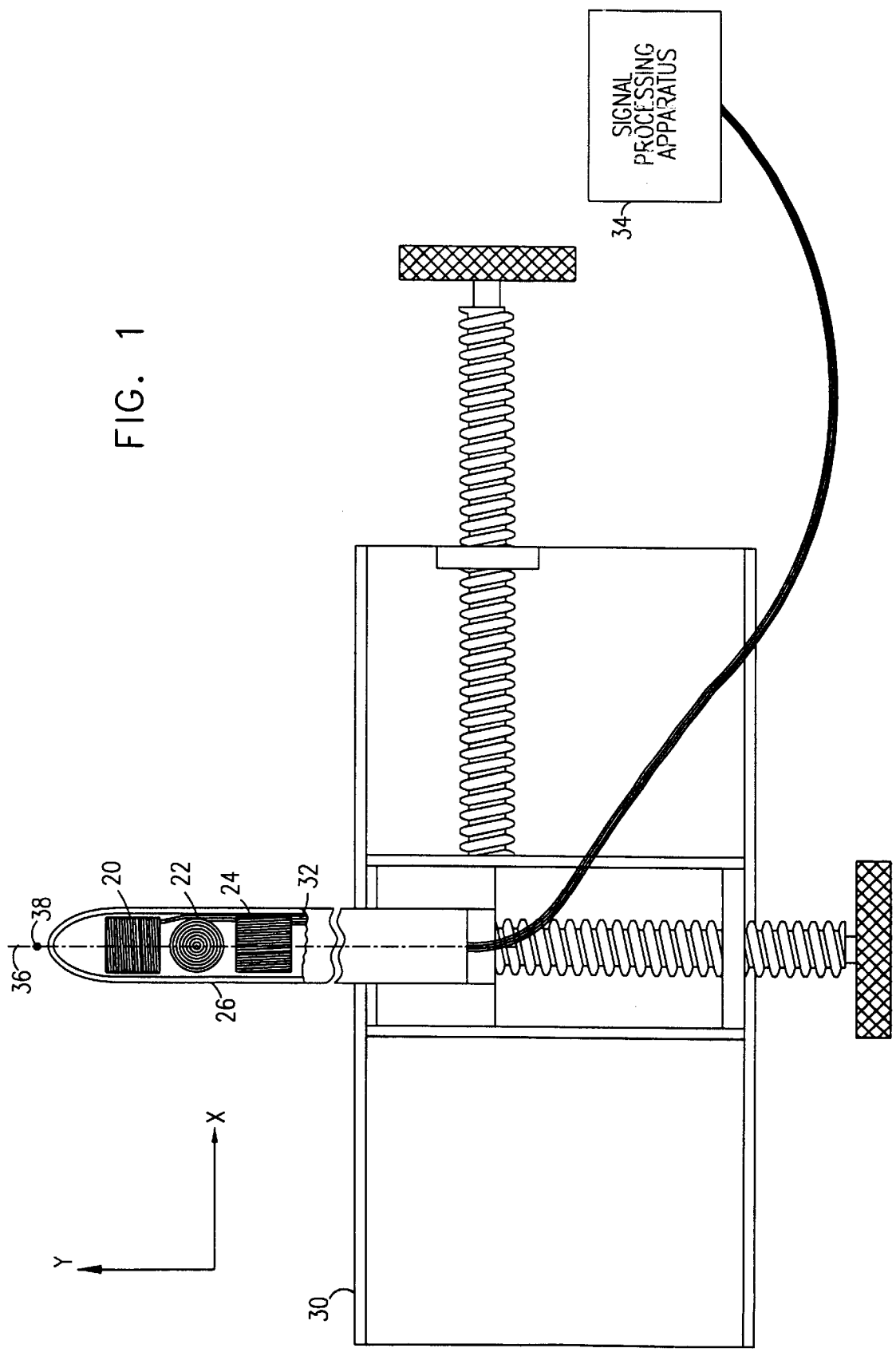
FIG. 1 is a schematic illustration of apparatus for calibrating a magnetic field generator, in accordance with a preferred embodiment of the present invention.

Reference is now made to FIG. 1, which shows three sensor coils 20, 22, 24 for calibrating a magnetic field generator (not shown in FIG. 1). Coils 20, 22 and 24 are preferably of small size, each coil having a volume of approximately 1 mm$^3$. The coils are fixed in a substantially linear arrangement to probe 26, which is in turn fixed to positioning device 30. Probe 26 and associated parts are preferably made from rigid plastic or other non-conducting substance, so as not to distort the lines of magnetic field. Coils 20, 22 and 24 are preferably oriented in predetermined, known orientations, which are mutually substantially orthogonal. In the presence of a time-varying magnetic field, electrical currents are induced in the coils, which are substantially proportional to the amplitudes of the components of the magnetic field along the coils' respective axes at their respective positions. These signals are conveyed by wires 32 to signal processing apparatus 34, which processes the signals to determine the direction and amplitude of the magnetic field.

In the preferred embodiment of the present invention shown in FIG. 1, positioning device 30 is an X–Y translation stage, which may be of any suitable type known in the art. In other preferred embodiments of the present invention, positioning device 30 may be an X–Y–Z translation device, or it may also include one or more rotation elements. Device 30 may be manually operated, motorized, or actuated using other means and methods known in the art, for example, by a robot.

The positions of coils 20, 22 and 24 on probe 26 define an axis of motion 36, which is parallel to the Y-direction as illustrated in FIG. 1. In a preferred embodiment of the present invention, positioning device 30 is adapted so as to move probe 26 along axis 36. Preferably device 30 moves probe 26 in steps of constant size, such that the distance between any pair of coils 20, 22 and 24 is an integral number of the steps. In this way, each of coils 20, 22 and 24 is positioned at each point along the axis, for example point 38, in turn, so that three substantially orthogonal components of the magnetic field are determined at each such point.

After magnetic fields have been measured at all desired points along axis 36, positioning device 30 shifts probe 26 by a predetermined, known distance in the X-direction, and then measurements are repeated by moving the probe along the Y-direction, as described above.

In another preferred embodiment of the present invention (not shown in the figures), the three non-concentric coils 20, 22 and 24 are fixed in a probe substantially as described in the above-mentioned PCT patent application No. PCT/US95/01103. This probe is fixed to a positioning device, and is used in place of probe 26 and coils 20, 22 and 24 in calibrating a radiator coil, as described above.

In still other preferred embodiments of the present invention, one, two, four or more coils, in any suitable geometrical configuration, may be used to calibrate a magnetic field generator. The coils may be concentric or non-concentric.

Figure 2A:
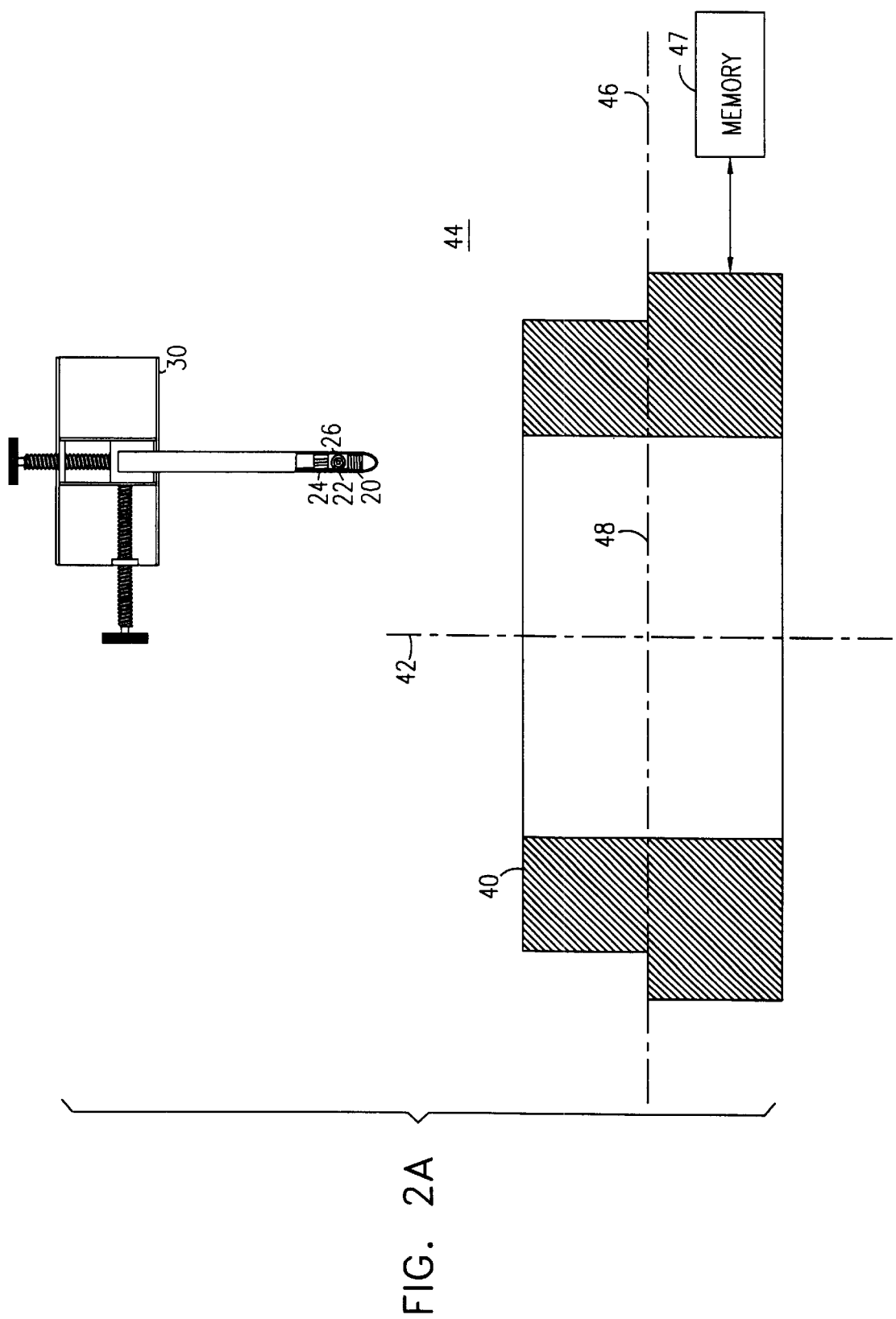
FIG. 2A is a schematic, sectional view of a magnetic field generator coil with an air core, for purposes of illustrating calibration of the coil, in accordance with a preferred embodiment of the present invention.

FIG. 2A is a sectional view of a radiator coil 40 having an air core 43 used in generating magnetic fields. Radiator coil 40 is rotationally symmetrical about symmetry axis 42. A second axis 46 is chosen to be orthogonal to symmetry axis 42, wherein second axis 46 is preferably located in a plane 48 defined by coil 40. Axes 42 and 46 define a quadrant 44 of a plane normal to plane 48. It will be appreciated by those skilled in the art that the magnetic fields generated by radiator coil 40 will also be rotationally symmetrical about axis 42. Thus, the directions and amplitudes of a magnetic field generated by coil 40, determined in relation to a quadrant 44, are substantially independent of the choice of second axis 46.

Therefore, in preferred embodiments of the present invention, radiator coil 40 is calibrated by measuring the direction and amplitude of the magnetic field at one or more points in quadrant 44 defined by axes 42 and 46. The measured values of direction and amplitude at the one or more points in this quadrant are then compared with theoretically calculated values, and any substantial differences between measured and theoretical values are recorded and used to determine calibration correction factors. In a preferred embodiment of the present invention, the calibration correction factors are stored electronically in a memory 47, preferably comprising an EPROM, or other programmable microcircuit, associated with the radiator coil. The correction factors determined in relation to quadrant 44 are subsequently applied to calibrate the magnetic field in all quadrants above plane 48 of the coil.

It will be appreciated that the method described above may equally be applied to determine calibration correction factors in relation to quadrants below plane 48 of coil 40. Furthermore, if the coil is additionally symmetrical under reflection in plane 48, the correction factors determined in relation to quadrant 44 will themselves be sufficient to determine calibration correction factors in relation to quadrants below the plane.

Figure 2B:
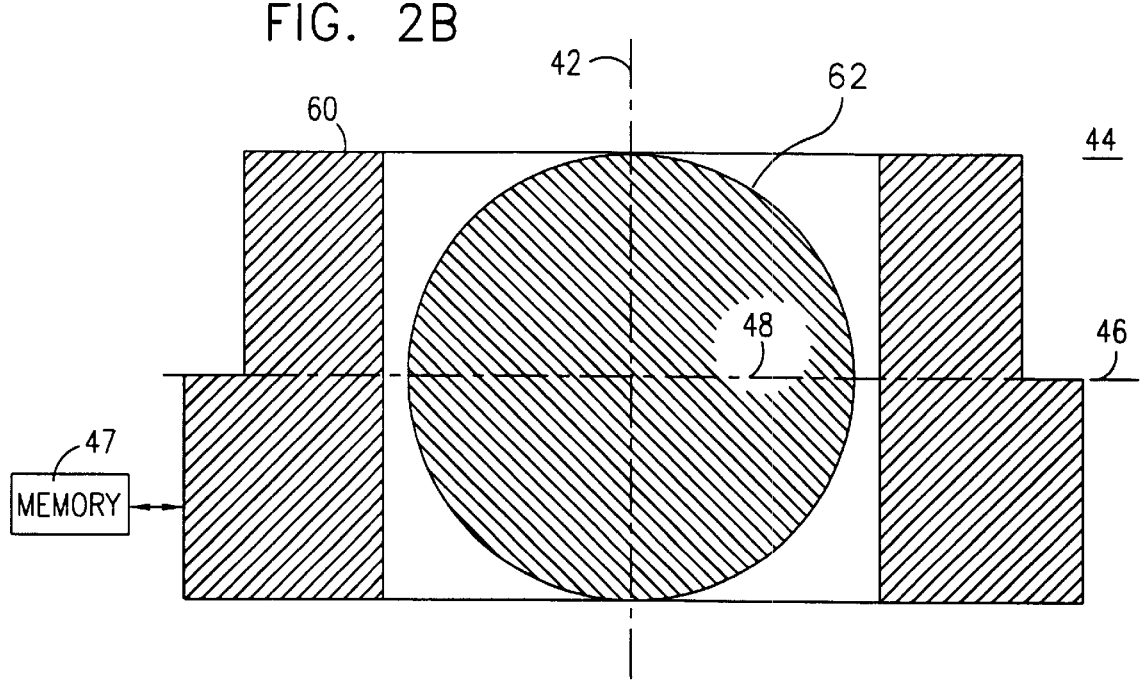
FIG. 2B is a schematic, sectional view of a magnetic field generator coil with a ferromagnetic core; for purposes of illustrating calibration of the coil, in accordance with a preferred embodiment of the present invention.

FIG. 2B is a sectional view of a radiator coil 60 used in generating magnetic fields. Coil 60 is substantially similar to coil 40, as described above, except that coil 60 contains a ferromagnetic core 62. Generally ferromagnetic core 62 will be formed from a non-conductive material such as a ferrite, or a conductive material such as soft iron. Ferromagnetic core 62 is rotationally symmetrical about symmetry axis 42. It will thus be appreciated that the magnetic fields generated by radiator coil 60 and ferromagnetic core 62 will also be rotationally symmetrical about axis 42. Thus, the directions and amplitudes of a magnetic field generated by coil 60 with core 62, determined in relation to a quadrant 44, are substantially independent of the choice of second axis 46 defined as above, so long as the symmetry is maintained.

The presence of ferromagnetic core 62 in coil 60 significantly enhances the amplitude of the magnetic field produced at a given position, compared to the field produced if no core is in place. The enhancement of the amplitude of the field enlarges the region, known as the mapping volume, in which sensor coils, for example, as described in the above-mentioned U.S. Pat. No. 5,391,199, give a sufficiently strong signal to enable accurate position measurements to be made.

Although the ferromagnetic core 62 increases the mapping volume relative to the current applied to the coil 60, the simple situation described above regarding the form of the magnetic field and the calibration of the coil in the air core case becomes more complicated when a ferromagnetic core is present. The presence of the ferromagnetic core 62 may cause the field to deviate significantly from theoretical models due to core parameters such as permeability, resistivity, and hysteresis. If, for example, the ferromagnetic core 62 has a generally finite resistivity, as in the case of a soft iron core, time-dependent magnetic fields will introduce eddy currents in the core, which will significantly perturb the field. Furthermore, if the core is not precisely symmetrical or is not precisely centered in coil 60, the magnetic field will further deviate from the theoretical model.

Thus, in a preferred embodiment of the present invention, parameters such as permeability, resistivity, hysteresis, position, shape and dimensions of the ferromagnetic core 62 are used in deriving a theoretical model against which the field of coil 60 is calibrated. The model preferably further includes parameters such as the number of turns, current flow, and cross-sectional area of the radiator coil 60. It will be understood that the above parameters of the coil and core are enumerated here by way of example, and other relevant parameters may similarly be included. The model is used to generate theoretical values of a vector magnetic field B (comprising components $B_r$, $B_\theta$, $B_\phi$) produced by radiator coil 60 and ferromagnetic core 62.

To calibrate coil 60, magnetic fields are measured at a plurality of points, preferably about 300 points, preferably as described above, and the measured magnetic field values obtained are compared with the theoretical values. Using multi-variable fitting methods known in the art, the measured data are used to calculate corrected, effective values of parameters such as permeability and an effective number of turns of the coil, for example. These effective parameter values may then be used in the theoretical model to calculate the magnetic field accurately anywhere in the mapping volume.

Figure 3:
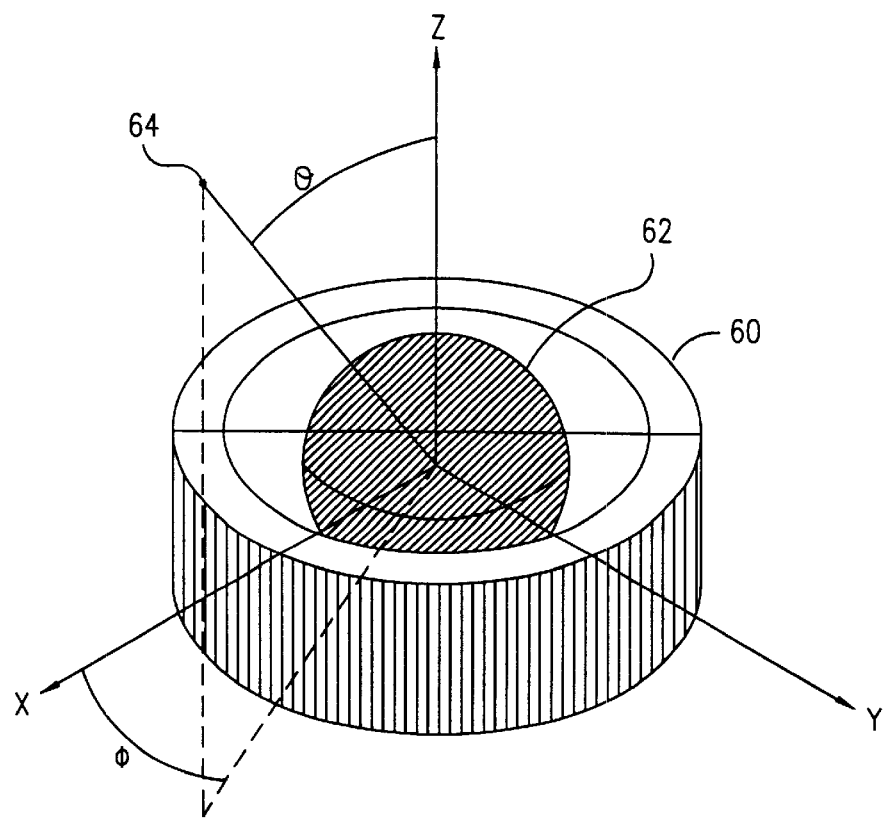
FIG. 3 is a schematic isometric illustration of a magnetic field generator coil with a ferromagnetic core, showing a coordinate system used in deriving a parametric model of the magnetic field due to the coil, in accordance with a preferred embodiment of the present invention.

FIG. 3 is an isometric view of coil 60, as shown in FIG. 2B, illustrating a coordinate system used in deriving the theoretical values of the magnetic field. Radiator coil 60 is assumed to comprise n turns of wire having a radius a and having a current I flowing in the wire. Ferromagnetic core 62 is assumed to be a sphere having a radius b and having a permeability $\mu$. As described in the above-mentioned text by Jackson, the theoretical field added to radiator coil 60 at point 64 by the presence of core 62 is generally given by:

$$B_r = \sum_{l=0}^{\infty} -B_l r^{-(l+2)}(l+1)P_l(\cos\theta) \quad (1)$$

$$B_\theta = \sum_{l=0}^{\infty} B_l r^{-(l+2)} P_l'(\cos\theta) \quad (2)$$

$$B_\phi = 0 \quad (3)$$

where $P_l(\cos\theta)$ and $P_l'(\cos\theta)$ are Legendre polynomials and their derivatives respectively, and $B_l = 0$ when l is even $$B_l = \frac{b^{3+2l}\left(\frac{b}{a}\right)^{2l} m(2b_l + c_l\mu + 2c_l l\mu)}{a^3(3+4l)\mu} \quad \text{when l is odd} \quad (4)$$

where the magnetic dipole moment m of the coil is given by:

$$m = \frac{n\pi a^2 I}{c} \quad (5)$$

where c is the velocity of light, and $$b_l = \frac{(-1)^l (2l+1)!!}{2^l l!} \quad (6)$$

and $$c_l = \frac{(-1)^l (2l+1)!!}{2^l (l+1)!} \cdot \frac{(2l+2)}{2l+1} \quad (7)$$

and $(2l+1)!! \equiv (2l+1)(2l-1)(2l-3)\ldots \times 5 \times 3 \times 1$.

These equations are preferably modified, using mathematical methods known in the art, for example, perturbation theory, to account for such effects as variations in permeability, eddy currents, hysteresis and other deviations of coil 60 and core 62 from theoretical behavior, as described above. The modified equations may be in the form of analytical solutions, similar to equations (1) through (4) and equations (6) and (7) above, with suitable changes. Alternatively, they may take the form of a numerical solution, calculated by a computer, with results dependent on the variably values of the coil and core parameters.

Figure 4:
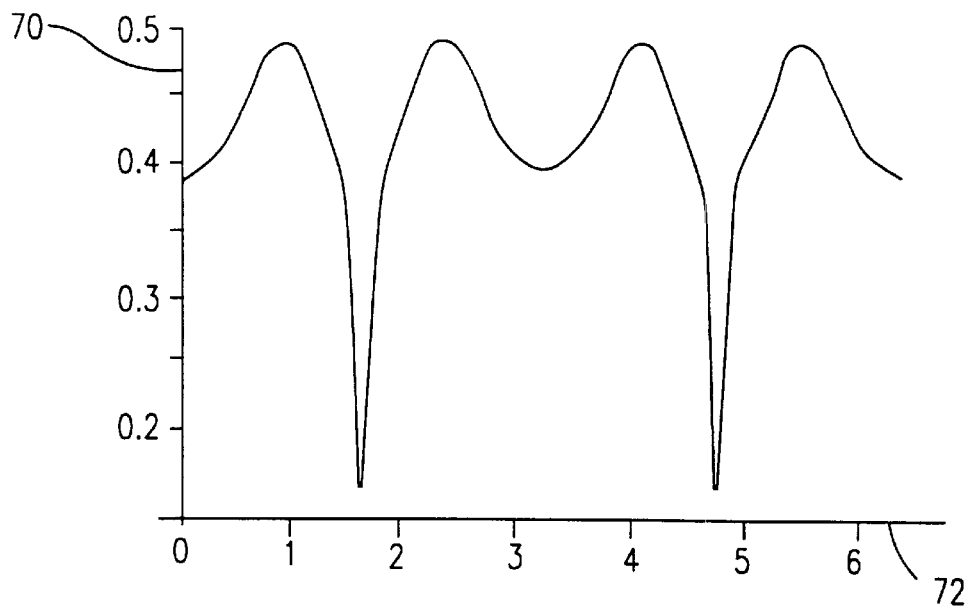
FIG. 4 is a graph illustrating a theoretical model of a magnetic field generated by the coil of FIG. 3.

FIG. 4 is a graph showing a cross section of the theoretical field added by the ferromagnetic core 62, at a distance of 25 cm from the center of the core in coil 60, as shown in FIG. 2B. The field is calculated using equations (1) through (7), above, by inserting typical values for the parameters: $\mu=1000$, a=5 cm and b=4.5 cm. Vertical axis 70 represents the fractional increase in the magnetic field magnitude, |B|, compared to the field with an air core, and horizontal axis 72 represents the angle $\theta$ measured in radians. It will be appreciated that changes in the values of the parameters used in the equations will result in changes in the shape of the curve in FIG. 4.

To calibrate coil 60, magnetic fields are measured at a plurality of points, using the system shown in FIG. 2A, for example. Using the fitting methods described above, parameters including an effective number of turns and an effective permeability are derived to give an optimal fitting of the curve shown in FIG. 4 to the measured values. These parameters are used in the equations above to calculate the magnetic field anywhere in the mapping volume. Alternatively, the parameters may be inserted into a numerical model for this purpose.

In preferred embodiments of the present invention, calibration of coil 40 with air core 43, or coil 60 with ferromagnetic core 62, is performed using the apparatus shown in FIG. 1, wherein coils 20, 22 and 24 on probe 26 are scanned mechanically by positioning device 30 through the one or more points in quadrant 44, as described above.

In an alternative preferred embodiment of the present invention, not shown in the figures, a two-dimensional array of sensor coils, in predetermined, known positions and orientations, is used to calibrate a magnetic field generator. For calibrating a rotationally symmetrical field generator, such as coil 40 with air core 43 shown in FIG. 2A, or coil 60 with ferromagnetic core 62 shown in FIG. 2B, the array is preferably positioned so that all the sensor coils in the array are located in quadrant 44. Thus, calibration correction factors may be determined substantially simultaneously for a substantial region of interest in the vicinity of the coil.

Figure 5:
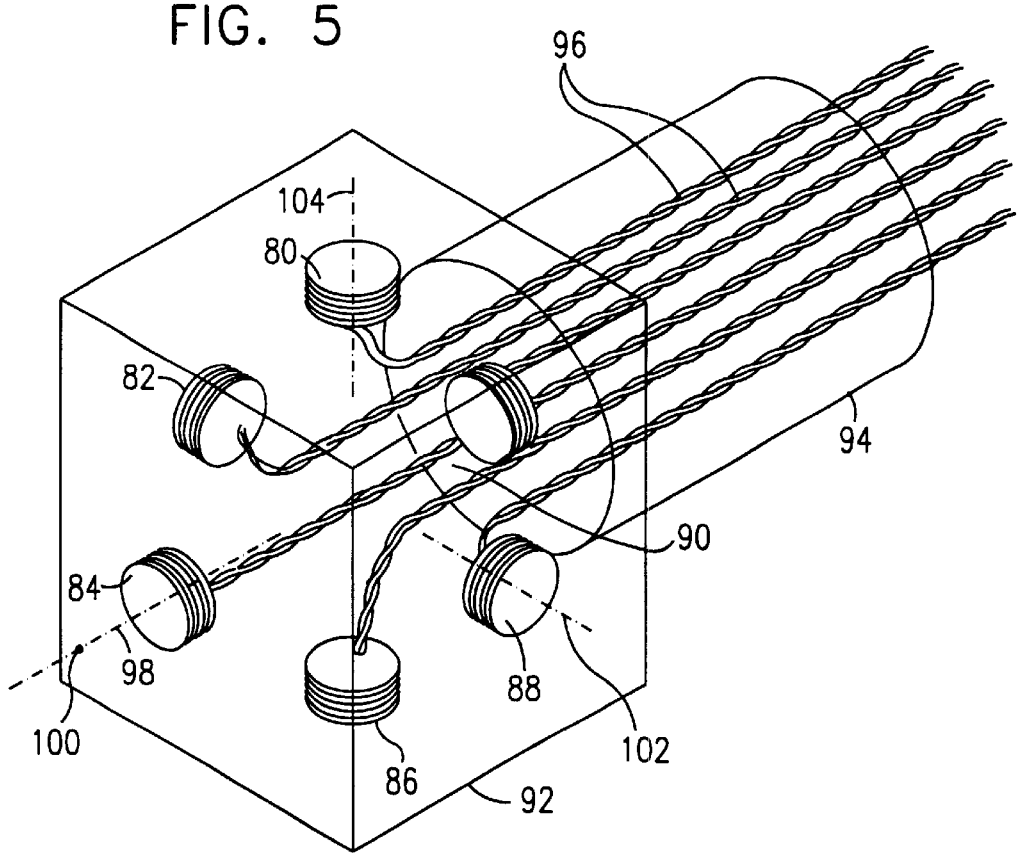
FIG. 5 is a schematic isometric illustration of apparatus for calibrating a magnetic field generator, in accordance with another preferred embodiment of the present invention.

FIG. 5 shows yet another alternative preferred embodiment for use in calibrating a magnetic field generator (not shown in FIG. 5), in accordance with a preferred embodiment of the present invention, comprising a cube 92 in which six sensor coils 80, 82, 84, 86, 88, 90 are fixed. The coils preferably have a diameter of approximately 1 mm and a height of approximately several millimeters, but they are enlarged in FIG. 5 for clarity. The coils are preferably fixed to the sides of a cube 92 so that: the axes of coils 80, 86 are substantially collinear and lie generally parallel to the X-direction shown in FIG. 5; the axes of coils 82, 88 are substantially collinear and lie generally parallel to the Z-direction; and the axes of coils 84, 90 are substantially collinear and lie generally parallel to the Y-direction. The three aforementioned axes are substantially orthogonal, and the coils are fixed to the sides of the cube so that the three axes intersect generally at the center of the cube.

Cube 92 has an edge length of approximately 3 cm, and the center-center distance of collinear coils is generally 2 cm. Cube 92 and associated parts are preferably made from rigid plastic or other non-conducting material, so as not to distort the magnetic field. In the presence of time-varying magnetic fields, signals from the coils are conveyed by wires 96 to signal processing equipment 34 (not shown in FIG. 5).

The centers of the coils 84 and 90 on cube 92 define an axis 98; the centers of the coils 80 and 86 on cube 92 define an axis 104; and the centers of the coils 82 and 88 on cube 92 define an axis 102. In a preferred embodiment of the present invention, cube 92 is set in positioning device 30 so that the edges of the cube are generally parallel to the X-, Y-, and Z-directions, and positioning device 30 moves cube 92 along axis 98. Preferably device 30 moves cube 92 in steps of constant size, such as 3 cm.

After magnetic fields have been measured at all desired points on axis 98, positioning device 30 shifts cube 92 by a predetermined, known distance such as 1 cm along axis 102, and then measurements are repeated by moving the probe parallel to the Y-direction, as described above. After magnetic fields have been measured at all desired points in the plane defined by axes 98 and 102, positioning device 30 shifts cube 92 by a predetermined, known distance such as 1 cm along axis 104, and then measurements are repeated by moving the probe parallel to the Y-direction, as described above. In this way coils 80 or 86, and coils 82 or 88, and coils 84 or 90, are positioned at each point, for example point 100, in turn, so that three substantially orthogonal components of the magnetic field are determined at each such point.

In some preferred embodiments of the present invention, radiator coil 40 with air core 43, or radiator coil 60 with ferromagnetic core 62, is used in a system for tracking the position and/or orientation of an object (not shown in the figures) in a vicinity of the coil. Preferably position-sensing coils are placed on or adjacent to this object, and generate electrical signals in response to a magnetic field generated by coil 40 or 60. The calibration correction factors determined in accordance with the above method are then applied to the electrical signals received from the position-sensing coils, so as to track the position and orientation of the object with greater accuracy.

In some such preferred embodiments of the present invention, the object being tracked is a catheter, for example, as described in the above-mentioned PCT patent application 01103 or in U.S. Pat. No. 5,391,199. Preferably, sensor coils 20, 22 and 24, which are used to calibrate radiator coil 40 or 60, are substantially similar to position-sensing coils adjacent to the distal end of the catheter.

In one such preferred embodiment of the present invention, signals received from these position-sensing coils are used to determine uncorrected position coordinates of the object, based on theoretical values of the amplitude and direction of the magnetic field generated by coil 40 or 60. Calibration correction factors determined for the position indicated by these uncorrected coordinates are applied so as to calculate corrected values of the magnetic field amplitude and direction in the vicinity of the object. The corrected magnetic field amplitude and direction are then used to find corrected position coordinates of the object.

The calibration correction factors determined in accordance with preferred embodiments of the present invention are preferably stored in the form of a look-up table, comprising additive or multiplicative factors, which are applied in calculating corrected values of the magnetic field amplitude and direction and/or corrected position coordinates of the object. Correction factors for all points within a region in the vicinity of a field generator, wherein the direction and amplitude of the field have been measured at a plurality of such points, may be determined by methods of interpolation and curve fitting known in the art.

It will be appreciated that the preferred embodiments described above are cited by way of example, and the full scope of the invention is limited only by the claims.

What is claimed is:

1. A method for calibrating a magnetic field generator, comprising:
   fixing one or more magnetic field sensors to a probe in known positions and orientations;
   selecting one or more known locations in a vicinity of the magnetic field generator;
   driving the magnetic field generator so as to generate a magnetic field;
   moving the probe in a predetermined, known orientation to each of the one or more locations;
   receiving signals from the one or more sensors at each of the one or more locations;
   processing the signals to measure the amplitude and direction of the magnetic field, at the respective positions of the one or more sensors; and
   determining calibration factors relating to the amplitude and direction of the magnetic field in the vicinity of the magnetic field generator.

2. A method according to claim 1, wherein fixing one or more magnetic sensors to a probe comprises fixing sensor coils to the probe.

3. A method according to claim 2, wherein fixing the sensor coils to the probe comprises fixing two or more sensor coils in orientations such that respective axes of the coils are mutually substantially orthogonal.

4. A method according to claim 3, wherein fixing the one or more magnetic sensors to a probe comprises fixing three sensors to the probe, such that the positions of the sensors on the probe are substantially collinear.

5. A method according to claim 3, wherein fixing the one or more magnetic sensors to the probe comprises fixing sensors to a cube.

6. A method according to claim 5, wherein selecting one or more known locations comprises selecting a plurality of locations, and wherein moving the probe comprises moving the probe along an axis defined by the one or more sensors on the probe and passing through two or more of the plurality of locations.

7. A method according to claim 6, wherein moving the probe along the axis comprises moving the probe in steps of substantially equal length, such that the distance between any two of the sensors is substantially integrally divisible by the length of the steps.

8. A method according to claim 7, where calibrating the magnetic field generator comprises calibrating a field generator that is substantially rotationally symmetrical, and
   wherein selecting the one or more known locations comprises selecting one or more locations in a quadrant defined by the axis of rotational symmetry of the magnetic field generator and by a second axis in a plane defined by the magnetic field generator and normal to the axis of rotational symmetry, and
   wherein moving the probe comprises orienting the probe so that the one or more sensors are positioned in the plane.

9. A method according to claim 8, wherein determining calibration factors comprises:
   calculating theoretical values of the amplitude and direction of the magnetic field generated by the magnetic field generator at the one or more known locations;
   comparing the theoretical values to the amplitude and direction of the magnetic field measured at said locations; and
   computing arithmetic factors based on the difference between the theoretical values and the measured amplitude and direction of the magnetic field at each such location.

10. A method according to claim 9, wherein computing arithmetic factors comprises fitting the theoretical values to the measured amplitude and direction of the field.

11. A method according to claim 10, wherein calculating theoretical values comprises:
   deriving a theoretical model of the magnetic field in the presence of an air core within the magnetic field generator; and
   modifying the model to account for the presence of a ferromagnetic core within the magnetic field generator.

12. A method according to claim 11, wherein modifying the model comprises determining a perturbation of the field due to the core.

13. A method according to claim 12, wherein determining the perturbation of the field comprises determining a perturbation due to a nonlinearity of the core.

14. A method according to claim 13, wherein determining the perturbation of the field comprises determining a perturbation due to eddy currents in the core.

15. A method according to claim 14, and comprising:
- fixing a magnetic-field-responsive position-sensing device to an object;
- placing the object in the vicinity of the magnetic field generator;
- receiving signals from the position-sensing device;
- processing the signals so as to calculate the position or orientation of the object; and
- applying the calibration factors so as to improve the accuracy of calculation of the position or orientation.

16. A method according to claim 15, and comprising storing the calibration factors in a memory associated with the radiator coil.

17. Apparatus for calibrating a magnetic field generator comprising:

- a plurality of magnetic field sensors, which generate electrical signals in response to magnetic fields applied thereto by the field generator;
- a positioning device, for moving the sensors;
- wherein the positioning device has an axis of motion that is parallel to an axis defined by two or more of the plurality of the coils, the magnetic field sensors comprising sensor coils, which are fixed so that respective axes of the coils are mutually substantially orthogonal, the sensors being fixed to the positioning device in a substantially linear arrangement, wherein the sensors are fixed to the faces of a cube, which is fixed to the positioning device; and
- a computer, which receives the signals from the sensors and compares them to a theoretical model, so as to calibrate the magnetic field generator.

* * * * *